(12) United States Patent
Suzuki

(10) Patent No.: US 9,271,642 B2
(45) Date of Patent: Mar. 1, 2016

(54) OPHTHALMOLOGY APPARATUS AND METHOD OF CONTROLLING OPHTHALMOLOGY APPARATUS

(71) Applicant: CANON KABUSHIKI KAISHA, Tokyo (JP)

(72) Inventor: Kei Suzuki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 29 days.

(21) Appl. No.: 14/102,337

(22) Filed: Dec. 10, 2013

(65) Prior Publication Data

US 2014/0168604 A1 Jun. 19, 2014

(30) Foreign Application Priority Data

Dec. 14, 2012 (JP) .................. 2012-273640

(51) Int. Cl.
*A61B 3/14* (2006.01)
*A61B 3/10* (2006.01)
(52) U.S. Cl.
CPC .................. *A61B 3/1015* (2013.01); *A61B 3/14* (2013.01)
(58) Field of Classification Search
CPC ................... A61B 3/14; A61B 3/152

USPC .................................................. 351/206, 208
See application file for complete search history.

(56) References Cited

U.S. PATENT DOCUMENTS

| 2011/0013139 A1* | 1/2011 | Bar et al. .................. 351/206 |
| 2011/0051089 A1* | 3/2011 | Wada et al. ................. 351/208 |
| 2011/0116044 A1* | 5/2011 | Nozato et al. ................ 351/206 |
| 2012/0242872 A1 | 9/2012 | Nozato et al. |
| 2014/0055748 A1* | 2/2014 | Saito ........................... 351/206 |

OTHER PUBLICATIONS

Zhang, et al., "High-speed volumetric imaging of cone photoreceptors with adaptive optics spectral-domain optical coherence tomography", Optics Express, May 15, 2006, pp. 4380-4394, vol. 14, No. 10.

* cited by examiner

*Primary Examiner* — Mahidere Sahle
(74) *Attorney, Agent, or Firm* — Canon USA Inc. IP Division

(57) ABSTRACT

An ophthalmology apparatus includes: an aberration measuring unit configured to measure an aberration of an eye to be examined on the basis of returned light from the eye to be examined irradiated with measurement light, and a change unit configured to change a size of an irradiating area in the aberration measurement unit to be irradiated with the returned light.

15 Claims, 5 Drawing Sheets

OPHTHALMOLOGY APPARATUS AND METHOD OF CONTROLLING OPHTHALMOLOGY APPARATUS

BACKGROUND OF THE INVENTION

1. Field of the Invention

This disclosure relates to an ophthalmology apparatus configured to measure an aberration of an eye to be examined and a method of controlling the ophthalmology apparatus.

2. Description of the Related Art

Examples of known ophthalmology apparatuses in recent years include a scanning laser ophthalmoscope (SLO) apparatus configured to scan a fundus two-dimensionally with a laser beam and acquire two-dimensional images of the fundus by receiving reflected light from the fundus, and an optical coherence tomography (OCT) configured to acquire a tomographic fundus image by using interference of low-coherence light. Examples of types of the OCT mainly include Time Domain OCT (TD-OCT) or Fourier Domain OCT (FD-OCT). Examples of the FD-OCT include Spectral Domain OCT (SD-OCT) and a Swept Source OCT (SS-OCT).

In such an ophthalmology apparatus, improvement in resolution by means of increased NA of a laser irradiation optical system is now in progress in recent years. At this time, since measurement light needs to pass through an optical tissue of an eye such as a cornea and a crystalline lens, and hence an image quality of a fundus image may be lowered due to an influence of an aberration of the cornea or the crystalline lens. Accordingly, The AO-SLO and the AO-OCT including an adaptive optics (AO) configured to measure an aberration of the eye and adapt the aberration integrated therein is disclosed in Y. Zhangetal, Optics Express, Vol. 14, No. 10, 15 May 2006. When measuring an aberration of an eye, Shack Hartman wave-front sensor system is generally employed. This system focuses a laser onto a retina of an eye and irradiates the retina therewith. Subsequently, part of reflected and scattering light from the retina, which has passed through the pupil and emitted from the pupil, is received by a sensor such as a CCD camera through a micro lens array, and on the basis of the received light, measurement of the wave front on the basis of the received light is enabled. Then, a variable mirror of a wave-front correction device of a spatial phase modulator is driven to correct the measured wave front. Accordingly, photographing of the fundus with high resolution is achieved.

SUMMARY OF THE INVENTION

This disclosure is intended to correct an aberration accurately by performing accurate alignment between an AO optical system and an eye to be examined.

There is provided an ophthalmology apparatus including:

an aberration measurement unit configured to measure an aberration of an eye to be examined on the basis of returned light from the eye to be examined irradiated with measurement light; and a change unit configured to change a size of an irradiating area in the aberration measurement unit which is irradiated with the returned light.

Further features of the present invention will become apparent from the following description of exemplary embodiments with reference to the attached drawings.

DESCRIPTION OF THE EMBODIMENTS

Modes of implementing this disclosure will be described on the basis of the following embodiments. However, this disclosure is not limited thereto.

When measuring an eye to be examined or acquiring an image of a fundus of the eye to be examined, alignment of an eye to be examined and an ophthalmology apparatus is required. In general, a method of irradiating an anterior eye with an alignment light from an optical system (camera) for alignment and performing the above-described alignment while confirming a corneal reflection bright point with an anterior eye camera is conceivable.

However, even when the optical system for alignment-specific optical system is accurately aligned with the eye to be examined, the AO optical system (optical systems including Shack Hartman wave-front sensor), which is different from the alignment-specific optical system, is not necessarily aligned with the eye to be examined due to an influence of a tolerance or the like at the time of assembly of the ophthalmology apparatus. In this manner, when the above-described alignment is performed by using the optical system different from the AO optical system, an accurate correction of the aberration may become difficult depending on the accuracy of the alignment between the AO optical system and the eye to be examined.

Figure 3A:
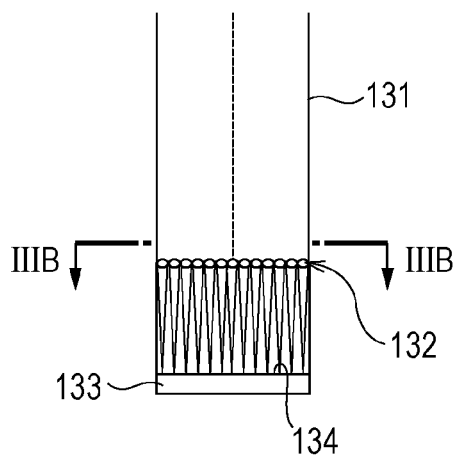
FIGS. 3A to 3F are schematic drawings for explaining a wave-front sensor of the first embodiment.
Figure 3B:
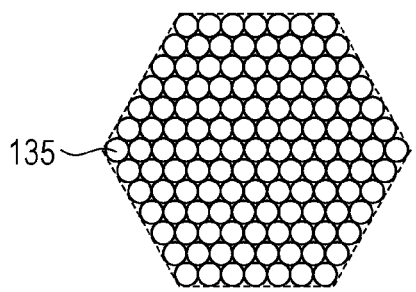
Figure 3C:
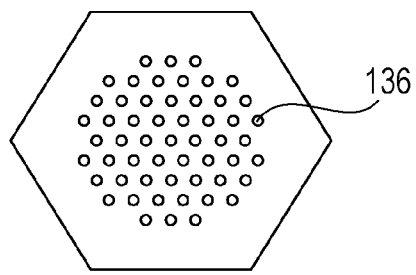
Figure 3D:
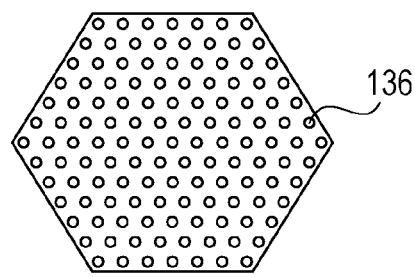

When the above-described wave-front sensor receives light, a circular bright portion corresponding to a pupil of the eye to be examined (see FIG. 3C illustrating Shack Hartman wave-front sensor) is acquired. An accurate alignment is achieved by causing the circular bright portion to come to a substantially center of the wave-front sensor. However, in a case where the pupil of the eye to be examined is large or a case of a mydriatic eye, the entire wave-front sensor corresponds to the bright portion (see FIG. 3D illustrating Shack Hartman wave-front sensor), and hence the alignment by using the bright portion may become difficult.

In view of such circumstances, the embodiment disclosed here is intended to change the bright portion in an aberration measurement unit in order to achieve accurate alignment when performing an alignment of the AO optical system and the eye to be examined on the basis of a result of measurement achieved by using the aberration measurement unit such as a wave-front sensor.

In order to achieve the above-described object, the embodiment disclosed here changes a size of an irradiating area in the aberration measurement unit irradiated with returned light from the eye to be examined. Accordingly, since the size of the bright portion in the aberration measurement unit can be changed, an accurate alignment is achieved in a case of, for example, performing the alignment between the AO optical system and the eye to be examined on the basis of the result of measurement achieved by the aberration measurement unit such as the wave-front sensor.

First Embodiment

Figure 1:
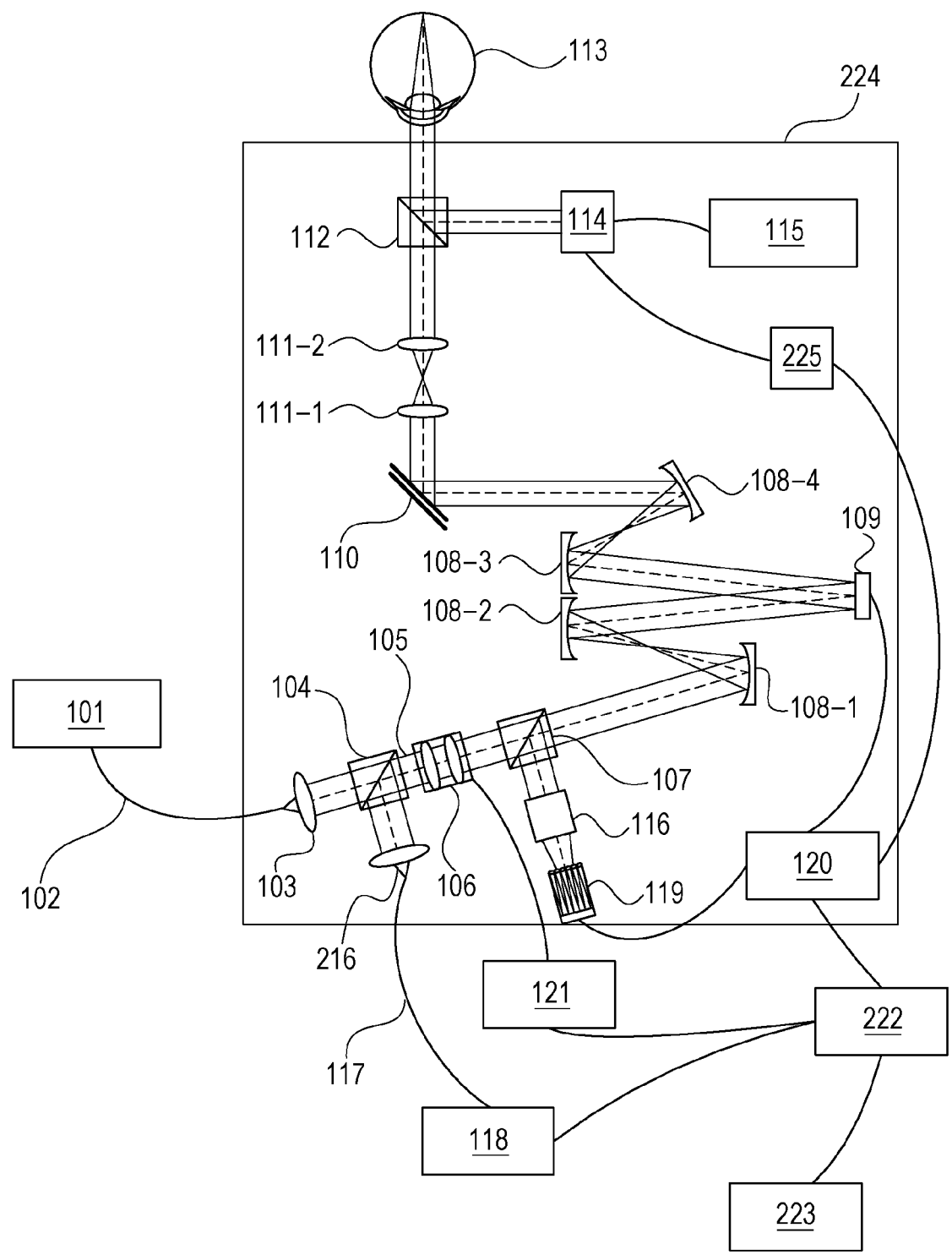
FIG. 1 is a schematic drawing for explaining an aberration measurement apparatus of a first embodiment.

FIG. 1 is a schematic drawing illustrating an example of an ophthalmology apparatus preferable for applying a first embodiment. This is an example of Scanning Laser Ophthalmoscope (SLO) with an adaptive optical system.

Reference numeral 101 denotes a light source, and an SLD power source (Super Luminescent Diode) having a wavelength of 840 nm is used. Although the wavelength of the light source 101 is not specifically limited, wavelengths in a range on the order from 800 to 1500 nm are preferably employed in order to reduce glare that a person being tested feels and maintain a resolution. In the first embodiment, the SLD power source is employed. However, laser or the like may be employed as well. In the first embodiment, a light source is commonly used for photographing a fundus and for measuring the wave front. However, a configuration in which separate light sources may be prepared respectively and waves are combined in a midcourse is also applicable.

First of all, light irradiated with the light source 101 passes through a single mode optical fiber 102, and is irradiated by a collimator 103 as a parallel light beam. Irradiated measurement light 105 passes through a beam splitter 104 as an example of a light split unit for acquiring an image of a fundus and enters a resolution changing unit 106.

Here, the resolution changing unit 106 is capable of changing the resolution by changing a diameter of an incident beam and outputting the beam. By changing the beam diameter on the order of a range from 7 mm to 1 mm, photographing with a resolution on the order from 3 μm to 20 μm above the fundus is achieved. It is effective to design the resolution to be variable in order to lower the resolution for suppressing data amount at the time of photographing at a wide field angle, to adjust the resolution in accordance with an aberration of an eye to be examined 113, or, depending on the photographing method, to photograph with a thin beam while avoiding a portion having a low transmissivity. A resolution changing unit 106 is controlled by a resolution control unit 121. The resolution control unit 121 is operated in cooperation with a control unit 222. The resolution changing unit 106 preferably has a configuration in which one of a plurality of optical members is inserted into an optical path or a configuration in which an aperture which can be changed in size is provided in the optical path, for example. Accordingly, a configuration in which the resolution is changed continuously or a configuration in which the resolution is changed discretely is applicable.

A measurement light 105 passing through the resolution changing unit 106 is guided to an adaptive optical system. The optical system of the adaptive optics includes a beam splitter 107 as an example of a light split unit for aberration measurement, a wave-front sensor 119 as an example of an aberration measuring unit, a wave-front correction device 109, and reflection mirrors 108-1 to 108-4 configured to guide light to these members. Here, the reflection mirrors 108-1 to 108-4 are installed so that at least a pupil of the eye to be examined 113, the wave-front sensor 119, and the wave-front correction device 109 are in an optical conjugate relation. In the first embodiment, a beam splitter is employed as the beam splitter 107. The measurement light 105 passing through the beam splitter 107 enters the wave-front correction device 109. The measurement light 105 reflected by the wave-front correction device 109 enters the reflection mirror 108-3.

The light reflected by the reflection mirrors 108-3 and 108-4 is one-dimensionally or two-dimensionally scanned by the scanning optical system 110. In the first embodiment, two Galvano scanners are used for primary scanning and secondary scanning. In order to achieve speedier photographing, a resonant scanner is used on the main scanning side of the scanning optical system 110 in some cases. Depending on the configuration, an optical element such as a mirror or a lens is used between the respective scanners in order to bring the respective scanners in the scanning optical system 110 into an optically resonant state in some cases. In the first embodiment, the scanning optical system 110 is a mechanism required when photographing an image of a fundus, and hence is kept standstill at a position at 0 degrees in scanning angle in the course of the aberration measurement. In order to correct various tolerances, the scanning optical system 110 may be kept standstill at a suitable offset angle.

The eye to be examined 113 is irradiated with the measurement light 105 scanned by the scanning optical system 110 through lenses 111-1 and 111-2 and a beam splitter 112, which is an example of a light split unit for observing the anterior eye. In the first embodiment, a perforated mirror or the like may be used as the beam splitter 112. The measurement light with which the eye to be examined 113 is irradiated is reflected or scattered by the fundus. Optimum irradiation is achieved by adjusting positions of the lenses 111-1 and 111-2. Although the lens is used in this embodiment, a spherical mirror or the like may be employed.

The anterior eye observation camera 114 observes the anterior eye through the beam splitter 112, and an appearance of the anterior eye of the eye to be examined 113 is displayed on a display 115. The appearance is memorized in a memory 225 as image data.

Reflected or scattering light (also referred to as "returned light") reflected or scattered from the retina of the eye to be examined 113 proceeds the same route as that the light has passed when entering in an opposite direction. Part of the returned light split by the beam splitter 107 passes through the variable power optical system 116 as an example of a change unit, with which the wave-front sensor 119 is irradiated, whereby the wave front of the light beam is measured. At this time, the light split unit for aberration measurement splits part of the returned light as light with which the aberration measurement unit is irradiated. The change unit is provided between the light split unit for aberration measurement and the aberration measurement unit.

In the first embodiment, since a case where acquisition of a fundus image and aberration measurement are executed on a real-time basis is assumed, part of the returned light is guided to the wave-front sensor 119 by the beam splitter 107. A reflecting member which can be inserted into the optical axis (for example, a flip up mirror) is conceivable as the beam splitter 107 other than the light split unit. In this case, the control unit 222 preferably controls aberration measurement to be performed in a state in which the reflection member is inserted into the optical path and, when the aberration measurement is terminated, controls the reflection member to move away from the optical path. Accordingly, when acquiring the image of the fundus, a loss of light amount in the returned light may be suppressed. In the configuration described above, the returned light which is guided to the wave-front sensor 119 may either be a part or the entirety as long as being at least part of the entirely.

Here, the variable power optical system 116 is capable of changing the thickness of the reflected or scattering light. Accordingly, the size of an irradiating area of the reflected or scattering light with which the wave-front sensor 119 is irradiated can be changed. In the first embodiment, a zoom lens is used as the variable power optical system 116. However, the embodiment is not limited thereto. For example, a configuration in which any one of a plurality of optical members having different powers is inserted into the optical path is also applicable. The change unit such as the variable power optical system 116 may have any configuration as long as the size of the irradiating area of the wave-front sensor 119 which is irradiated with the reflected or scattering light can be changed.

A state of light focusing of a CCD sensor of the wave-front sensor 119 may be displayed on a display 223. The reflected or scattering light passing through the beam splitter 107 is reflected partly by the beam splitter 104, and is guided to a light-intensity sensor 118 via a collimator 216 and an optical fiber 117. Light is converted into an electric signal by a light-intensity sensor 118, is formed into an image as an image of a fundus by the control unit 222, and is displayed on the display 223.

Wave-Front Correction Device

Figure 2A:
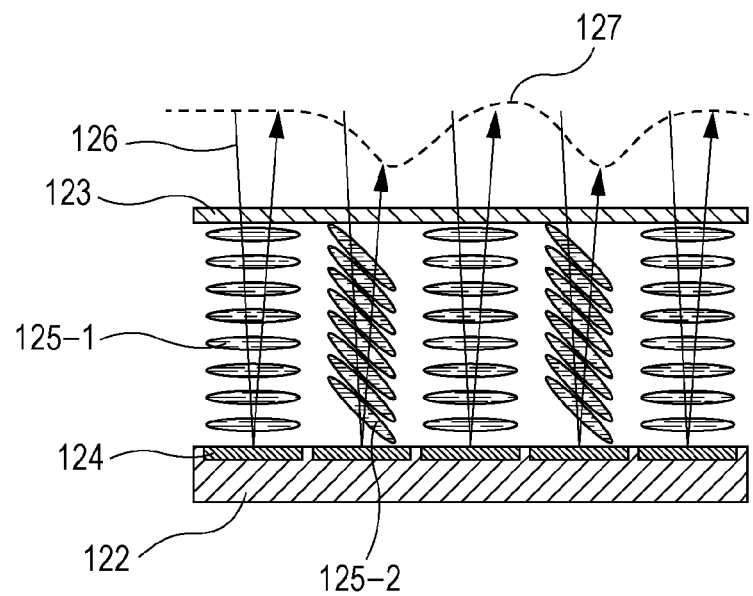
FIGS. 2A and 2B are schematic drawings for explaining a wave-front correction device of the first embodiment.

Here, in the first embodiment, a spatial phase modulator in which a liquid crystal device as a wave-front correction device 109 (also referred to as an aberration correction device) is used is employed. FIG. 2A illustrates a schematic drawing of a reflective liquid crystal light modulator. The reflective liquid crystal light modulator has a structure in which liquid crystal molecules 125-1 and 125-2 are enclosed in a space interposed between a base unit 122 and a cover 123. The base unit 122 has a plurality of pixel electrodes 124, and a cover 123 has a transparent counter electrode, not illustrated. In a case where no voltage is applied between the electrodes, the liquid crystal molecules are oriented as indicated by 125-1, and when a voltage is applied, the state of orientation is translated to a state indicated by 125-2, and a refractive index with respect to an incident light is changed. A spatial phase modulation is achieved by controlling the voltage of the respective pixel electrodes and changing refractive indexes of the respective pixels. For example, when the incident light 126 enters the modulator in question, light passing through the liquid crystal molecule 125-2 has a phase delay with respect to light passing through the liquid crystal molecule 125-1, and form a wave front illustrating in the drawing by reference numeral 127 as a consequence. In general, the reflective liquid crystal light modulator includes several tens of thousands to several hundreds of thousands of pixels. Also, since the liquid crystal device has a light-polarizing characteristic, there is a case where a polarizing element for adjusting polarized light of the incident light is included on an optical path of the incident light of the modulator.

Figure 2B:
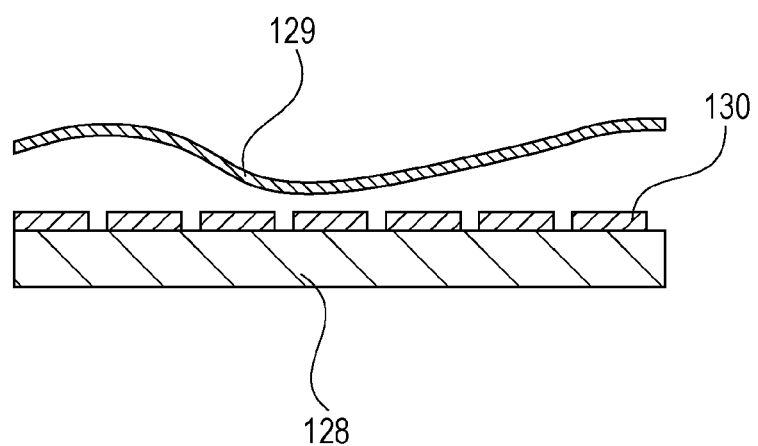

As another example of the wave-front correction device 109, there is a variable shape mirror. The variable shape mirror is configured to be capable of changing the direction of reflection locally, and those of various types are brought into practical use. For example, there is a device having a cross-section as illustrated in FIG. 2B. The device includes a deformable film-shaped mirror surface 129 configured to reflect an incident light, a base unit 128, actuators 130 arranged so as to be interposed therebetween, and a supporting portion, not illustrated, configured to support a mirror surface 129 from the periphery. Examples of operating principles of the actuators 130 include those utilizing an electrostatic force, a magnetic force, and a piezoelectric effect, and the configuration of the actuators 130 varies depending on the operation principles. A plurality of the actuators 130 are arranged two-dimensionally on the base unit 128, and are configured to be capable of deforming a mirror surface 129 by being selectively driven. In general, the variable shape mirror includes several tens to several hundreds of actuators.

Wave-Front Sensor

Here, the wave-front sensor 119 is irradiated with reflected of scattering light reflected from the reflection mirrors 108-2 and 108-1 and the beam splitter 107 in order to measure the wave front of the light beam. In the first embodiment, a Shack Hartman wave-front sensor is used as the wave-front sensor 119. FIG. 3A and FIG. 3B are schematic drawings illustrating the Shack Hartman wave-front sensor. Reference sign 131 denote a light beam used for measuring the wave-front and is focused on a focal plane 134 on a CCD sensor 133 through a micro lens array 132. FIG. 3B is a drawing illustrating an appearance viewed from IIIB-IIIB in FIG. 3A. A state in which the micro lens array 132 includes a plurality of micro lenses 135 is illustrated. The light beam 131 is focuses on the CCD sensor 133 through the micro lenses 135, and hence the light beam 131 is focused by being split into a plurality of spots of the micro lenses 135. Here, a state of being focuses on the CCD sensor 133 varies as illustrated in FIG. 3C and FIG. 3D depending on the magnitude relationship between the thickness of the reflected or scattering light (returned light) and the size of the wave-front sensor 119. The light beams passing through the respective micro lenses are focused on a spots 136. When the pupil of the eye to be examined is small, as illustrated in FIG. 3C, the thickness of the reflected and scattering light becomes smaller than the wave-front sensor 119. In such a case, an image received by the CCD sensor 133 becomes a circular bright portion corresponding to the pupil (also referred to as an irradiating area of the external lead 19 that is irradiated with the reflected or scattering light). In contrast, in a case where the diameter of the pupil of the eye to be examined is large (or mydriatic), the thickness of the reflected and scattering light becomes larger than the wave-front sensor 119. In this case, since the light is received by the entire surface of the CCD sensor 133, the bright portion has a shape corresponding to the entire surface.

Figure 3E:
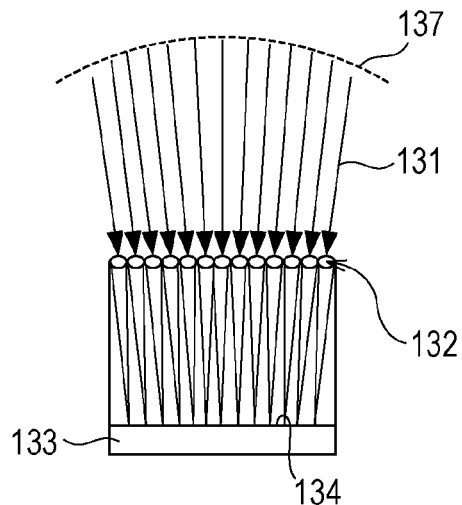
Figure 3F:
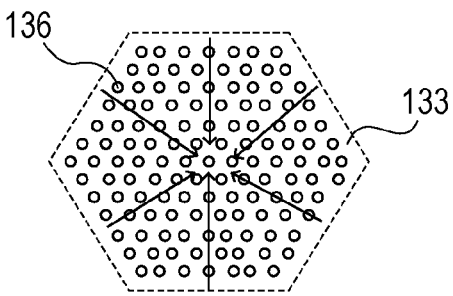

The calculation of the wave front of the incident light beam is performed on the basis of the positions of the respective spots 136 focused by the micro lenses. For example, FIG. 3E is a schematic diagram illustrating a case where the wave front having a spherical aberration is measured. The light beam 131 is formed with a wave front as illustrated by reference numeral 137. The light beam 131 is focused at a local perpendicular position of the wave front by a micro lens array 132. The focusing state of the CCD sensor 133 in this case is illustrated in FIG. 3F. Since the light beam 131 has a spherical aberration, the spots 136 are focused in a state of deviated to a center portion. By calculating these positions, the wave front of the light beam 131 is obtained. The wave-front sensor which can be applied to this disclosure is not limited to the Shack Hartman wave-front sensor, but any type is applicable as long as it can measure the wave front. For example, there is a wave-front curvature sensor, which is capable of measuring wave-fronts on the basis of variations in light brightness distribution before and after in the direction of travel of the light.

The wave-front sensor 119 is connected to an adaptive optical control unit 120, and transmits the received wave front to the adaptive optical control unit 120. The wave-front correction device 109 is also connected to the adaptive optical control unit 120, and performs a modulation instructed by the adaptive optical control unit 120. The adaptive optical control unit 120 calculates the amount of modulation which corrects the wave front to a wave front having no aberration on the basis of the wave front acquired from the wave-front sensor 119, and issues a command to the wave-front correction device 109 so as to modulate as being instructed. The measurement of the wave front and instruction issued to the wave-front correction device 109 are repeatedly processed, and feedback control is performed to always obtain an optimum wave front.

Flow of Aberration Measurement

Figure 4:
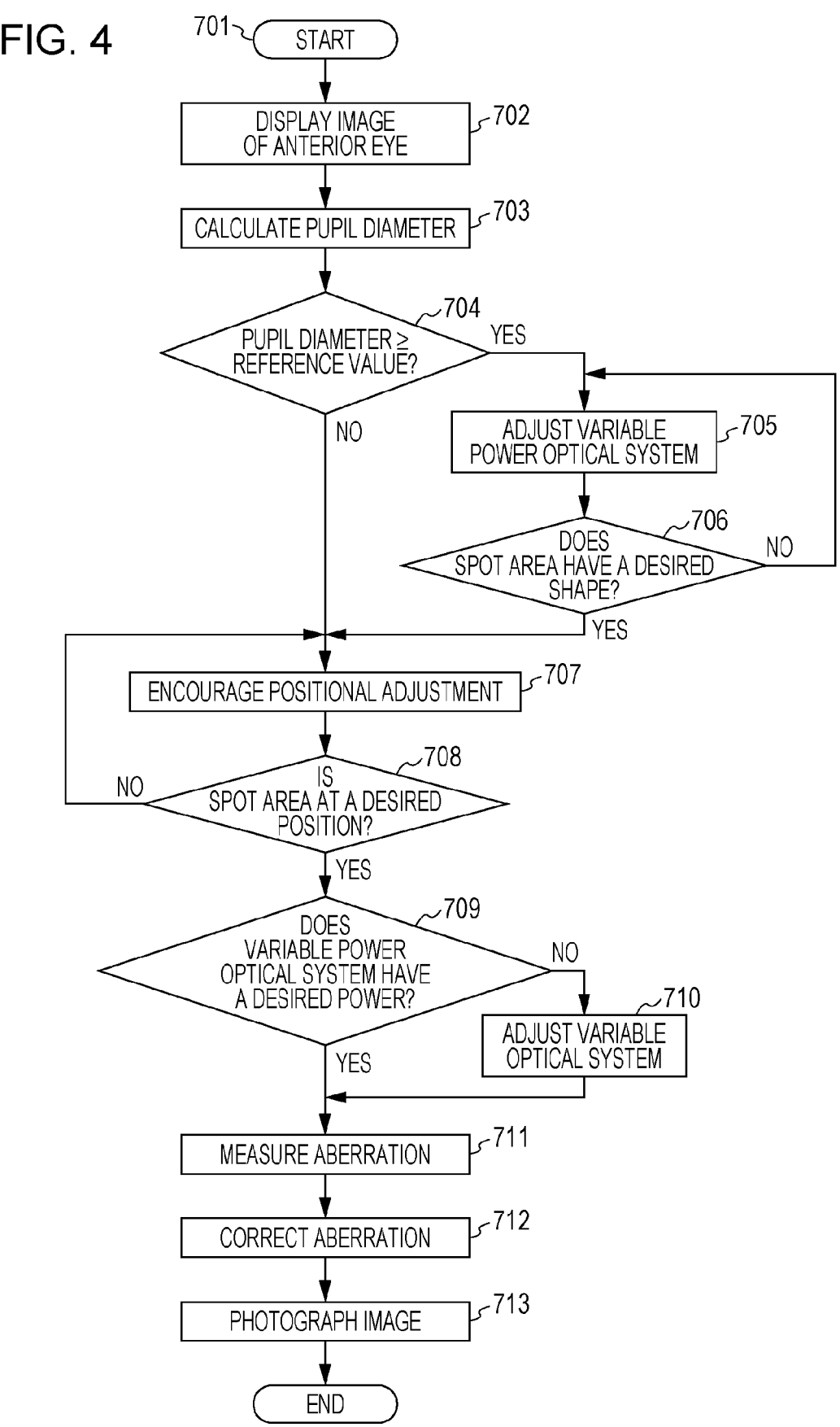
FIG. 4 is a flowchart illustrating an example of a control step of the first embodiment.

Subsequently, a flow of the measurement in the first embodiment will be described with reference to a flowchart illustrated in FIG. 4. First of all, in Step 701, the control unit 222 starts control. In Step 702, the control unit 222 as an example of a display control unit, not illustrated, causes an observed image of an anterior eye to be displayed on the display 115. Also, the control unit 222 stores the observed image of anterior eye as image data in a memory 225. In Step 703, the control unit 222 extracts a pupil area of the eye to be examined 113 from the image of the anterior eye stored in the memory 225 by the control unit 222. Also, the control unit 222 detects a pupil diameter of the eye to be examined 113 on the basis of the extracted pupil area. When detecting the pupil diameter of the eye to be examined 113, for example, the pupil diameter is calculated from a meridian direction to another, and an average value of the result of detection is employs as a pupil diameter. The value to be obtained does not necessarily have to be the pupil diameter, and the size of the pupil, for example, the surface area of the pupil is also applicable. In Step 704, whether or not the detected pupil diameter is a reference value (threshold value) or higher is determined. This determination may be performed by an operator, or by the control unit 222 performing a comparison between the detected pupil diameter and the reference value. When the detected pupil diameter is lower than the reference value, a process from Step 707 onward is executed. Also, when the detected pupil diameter is equal to or higher than the reference value, the procedure goes to Step 705. Here, the reference value is determined from a relationship between the magnitude of the CCD sensor 133 and the optical system, and it is assumed to be 4 mm in the first embodiment.

In Step 705, the power of the variable power optical system 116 is adjusted so that the spot area as an example of irradiating area on the eye to be examined 113 of the wave-front sensor 119 is displayed in a state of a circle corresponding to the pupil as illustrated in FIG. 3C. The reason is that a spot area has a high probability of becoming larger than the CCD sensor 133 as illustrated in FIG. 3D when the pupil diameter is equal to or higher than the threshold value. The adjustment of the power may be performed manually by the operator, or may be performed automatically by controlling a drive mechanism (not illustrated) composed of a motor or the like. For example, an adjustment of the power so that the size of the irradiating area becomes a predetermined size (for example, a size within a range of the CCD sensor 133) is conceivable. Also, in Step 706, whether or not the adjustment of the power is completed is determined. This determination may be achieved by the operator or by the control unit 222 automatically by performing an image information process.

In Step 707, a display control unit, not illustrated, controls a display 223 to display a display form indicating the direction such as an arrow or the like on the display 223 so that the spot area on the CCD sensor comes to a predetermined position. Accordingly, the operator may be encouraged to adjust a relative position between the eye to be examined 113 and the optical unit 224 including an adaptive optical system or the like (the position of the optical unit 224 with respect to the eye to be examined 113 or the position of the eye to be examined 113 with respect to the optical unit 224). The display control unit may control the display 223 to display a display form indicating the center position of the spot area (for example, an alignment mark). Also, various offsets caused by the apparatus or the optical system of the eye to be examined may be added to display an alignment index which guides the spot area to the display 223. In Step 708, whether or not the spot area is at a predetermined position, that is, whether the positional relationship between the eye to be examined 113 and the optical unit 224 is at the predetermined position is determined. This determination may be performed by the operator, or may be made by the control unit 222 by no operation being performed by the operator for a certain period. When the spot area is at the predetermined position, whether or not the adjustment of the variable power optical system 116 is required is determined again in Step 709. This determination may be achieved by the operator or by setting a reference value of power in advance and comparing with the reference value by the control unit 222. When the re-adjustment is determined to be unnecessary, a process from Step 711 onward is executed. When the re-adjustment is determined to be necessary, the procedure goes to Step 710.

In Step 710, the power of the variable power optical system 116 is adjusted again. The power may be adjusted to a power in Step 705 (power before adjustment), or accuracy of the aberration measurement may be performed by increasing a factor. What is required is just to adjust to a predetermined power. The adjustment may be performed manually by the operator, or may be performed by controlling a drive mechanism (not illustrated) composed of a motor or the like. When the adjustment is completed, the procedure goes to aberration measurement in Step 711. Subsequently, aberration correction is performed in Step 712 on the basis of the value of measured aberration, and then photographing of the fundus is performed in Step 713.

In this manner, according to the first embodiment, highly precise alignment with respect to the optical system may be encouraged also for an eye to be examined having a large pupil or an enlarged pupil, whereby the highly precise aberration measurement is achieved. Also, by adding a variable power optical system, the configuration may be simplified.

Second Embodiment

In a second embodiment, a Scanning Laser opthalmoscope (SLO) is applied. A point different from the first embodiment is a configuration of the variable power optical system 116. Since the configuration except for the variable power optical system 116 is the same as that of the first embodiment, description will be omitted. In the second embodiment, the thickness of the returned light with which the CCD sensor 133 is irradiated may be changed by inserting and removing a reduction optical system as an example of the variable power optical system into and from the optical system. Accordingly, the size of the irradiating area on the CCD sensor 133 may be changed. This configuration will be described with reference to FIGS. 5A and 5B.

Figure 5A:
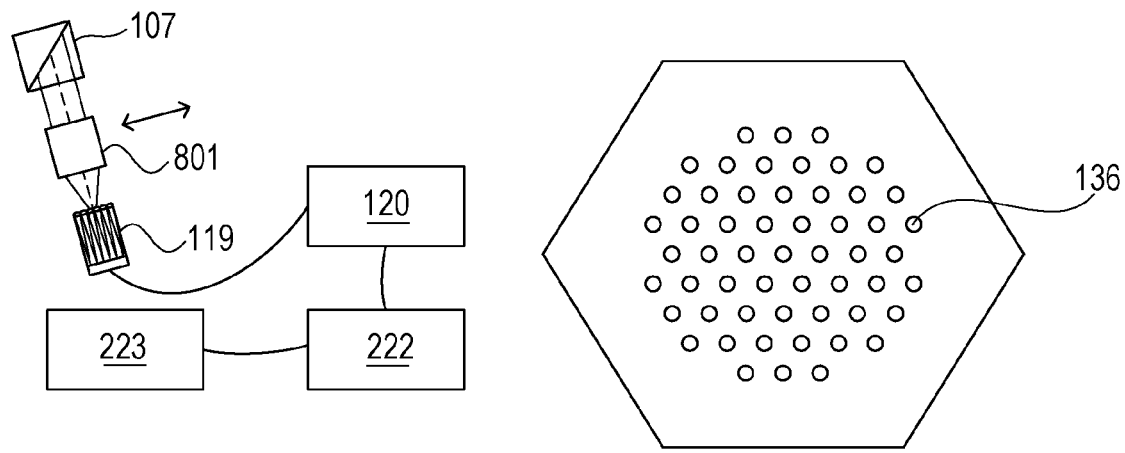
FIGS. 5A and 5B are schematic drawings for explaining part of an aberration measurement apparatus of a second embodiment.

First of all, FIG. 5A estimates a case of alignment between an eye to be examined and the optical unit 224. At this time, the reduction optical system 801 is inserted into the optical path. The reflected or scattering light with which the wave-front sensor 119 is irradiated may be thinned by the reduction optical system 801. Accordingly, even in a state in which the pupil of the eye to be examined 113 is large (or mydriatic), the spot area on the CCD sensor 403 is displayed in a state having a circular shape corresponding to the pupil as illustrated in FIG. 5A. Presence and absence of the reduction optical system 801 does not impact on an optical conjugate relation between the pupil of the eye to be examined and the wave-front sensor 119 or the wave-front correction device 109.

Figure 5B:
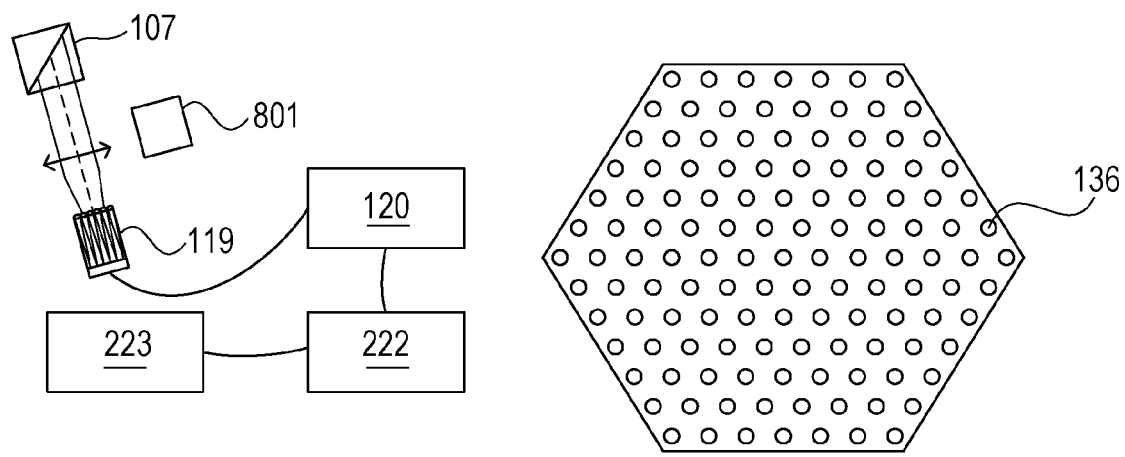

FIG. 5B illustrates an estimation of a case of measuring the aberration. At this time, the reduction optical system 801 is moved away from the optical path. When the spot area is adjusted to a predetermined position by the above-described alignment, the reduction optical system 801 is moved away from the optical path as illustrated in FIG. 5B. At this time, the reduction optical system 801 may be moved away from the optical path manually by the operator. Also, the control unit 222 may move the reduction optical system 801 away from the optical path automatically by a drive mechanism (not illustrated) including a motor, a solenoid, a cylinder, and the like. As a trigger when moving the reduction optical system 801 away from the optical path, determination of completion of the alignment between the eye to be examined 113 and the optical unit 224 by the control unit 222 is preferable. For example, it is conceivable that the spot area is adjusted to a predetermined position in the CCD sensor 133. In the second embodiment, the reduction optical system 801 is installed between the beam splitter 107 and the wave-front sensor 119. However, any position is applicable as long as it is between the eye to be examined 113 and the wave-front sensor 119. Also, when measuring the aberration and when acquiring an image, it is preferably not only to move the reduction optical system 801 away from the optical path, but also to insert an enlargement optical system (not illustrated). Accordingly, since the measurement area of the wave-front sensor 119 may be enlarged as much as possible as illustrated in FIG. 3D, the accuracy of the aberration measurement may be enhanced.

In this manner, according to the second embodiment, highly precise alignment between the eye to be examined and the optical system is also encouraged even for a state in which the pupil is large (or mydriatic). Accordingly, highly precise aberration measurement is achieved. In the second embodiment, the reduction optical system is employed. However, a configuration in which the enlargement optical system is inserted into or removed from the optical system is also applicable. In this case, it is preferable to move the enlargement optical system away from the optical path at the time of alignment, and insert the enlargement optical system into the optical path when measuring the aberration.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-273640, filed Dec. 14, 2012, which is hereby incorporated by reference herein in its entirety.

What is claimed is:

1. An ophthalmology apparatus configured to irradiate an eye to be examined with measurement light, to correct an aberration of returned light from the eye to be examined with a correction unit, and to acquire an image of the eye to be examined based on the corrected returned light, the apparatus comprising:
   a light split unit configured to split the corrected returned light into light for aberration measurement and light for forming an image of the eye to be examined;
   a change unit configured to change a beam diameter of the light for aberration measurement split by the light split unit;
   an aberration measurement unit configured to measure an aberration of the light for aberration measurement having passed through the change unit and having the beam diameter changed by the change unit; and
   a display control unit configured to control a display unit to display a display form indicating an irradiating area on the aberration measurement unit which is irradiated with the light,
   wherein the change unit is disposed in an optical path of the light for aberration measurement between the light split unit and the aberration measurement unit, and
   wherein the light for aberration measurement is incident on the aberration measurement unit after passing through the change unit.

2. The ophthalmology apparatus according to claim 1, wherein the display control unit controls the display unit to display the display form with an alignment index which guides the display form.

3. The ophthalmology apparatus according to claim 1, further comprising a control unit configured to control the change unit so as to increase the beam diameter of the light when alignment between the eye to be examined and an optical unit including the aberration measurement unit is completed, wherein
   the aberration measurement unit measures the aberration of the light having the changed beam diameter.

4. The ophthalmology apparatus according to claim 3, further comprising a drive unit configured to drive the optical unit with respect to the eye to be examined, and
   the control unit controls the drive unit so that the irradiating area comes to a predetermined position of the aberration measurement unit.

5. The ophthalmology apparatus according to claim 4, wherein the control unit controls the drive unit so that the irradiating area comes to the predetermined position of the aberration measurement unit after the beam diameter of the light has changed to a size within a measurable region of the aberration measuring unit by the change unit.

6. The ophthalmology apparatus according to claim 4, further comprising:
   an acquiring unit configured to acquire an image of an anterior eye of the eye to be examined; and
   a detection unit configured to detect a size of a pupil from the image of the anterior eye, wherein
   the control unit controls the drive unit after the change unit is controlled so that the irradiating area becomes smaller when the size of the pupil is equal to or larger than a threshold value.

7. The ophthalmology apparatus according to claim 1, wherein the change unit is provided on an optical path between the aberration measurement unit and the light split unit, and the change unit is a variable power optical system configured to change a beam diameter of the light.

8. The ophthalmology apparatus according to claim 1, further comprising a plurality of optical members configured to change the light into different beam diameters, wherein
the change unit is configured to change the beam diameter of the light by selectively inserting the plurality of optical members into and removing them from the optical path between the aberration measurement unit and the light split unit.

9. The ophthalmology apparatus according to claim 1, wherein the aberration measurement unit is a Shack Hartman wave-front sensor.

10. A method of controlling an ophthalmology apparatus which irradiates an eye to be examined with measurement light, corrects an aberration of returned light from the eye to be examined with a correction unit, and acquires an image of the eye to be examined based on the corrected returned light, the method comprising:
splitting, using a light split unit, the corrected returned light into light for aberration measurement and light for forming an image of the eye to be examined;
changing, using a change unit, a beam diameter of the light for aberration measurement split in the splitting step;
measuring, using an aberration measurement unit, the aberration of the light for aberration measurement having passed through the change unit and having the beam diameter changed in the changing step; and
displaying on a display unit a display form indicating an irradiating area on the aberration measurement unit which is irradiated with the light,
wherein the change unit is disposed in an optical path of the light for aberration measurement between the light split unit and the aberration measurement unit, and
wherein the light for aberration measurement is incident on the aberration measurement unit after passing through the change unit.

11. The method of controlling the ophthalmology apparatus according to claim 10, wherein
the display form is displayed on the display unit with an alignment index which guides the display form.

12. The method of controlling the ophthalmology apparatus according to claim 10, further comprising:
changing the beam diameter of the light into a size within a measurable region of the aberration measurement unit;
controlling a drive unit configured to drive the optical unit with respect to the eye to be examined so that the irradiating area changed in the size comes to a predetermined position of the aberration measurement unit; and
determining that the alignment is completed when the irradiating area comes to the predetermined position.

13. The method of controlling the ophthalmology apparatus according to claim 10, further comprising:
acquiring an image of an anterior eye of the eye to be examined;
detecting the size of the pupil from the image of the anterior eye;
reducing the size of the irradiating area when the size of the pupil is equal to or larger than a threshold value;
controlling a drive unit configured to drive the optical unit with respect to the eye to be examined so that the irradiating area reduced in the size comes to a predetermined position of the aberration measurement unit;
and
determining that the alignment is completed when the irradiating area comes to the predetermined position.

14. A program causing a computer to perform respective steps of the method of controlling the ophthalmology apparatus according to claim 10.

15. The ophthalmology apparatus according to claim 1, wherein, in the optical path from the light split unit to the aberration measurement unit, the light for aberration measurement passes only through the change unit prior to irradiating the aberration measurement unit.

* * * * *